US00PP14556P39

(12) United States Plant Patent
López

(10) Patent No.: US PP14,556 P3
(45) Date of Patent: Feb. 24, 2004

(54) NECTARINE TREE NAMED 'PLABLANEC'

(50) Latin Name: *Prunus persica*
Varietal Denomination: Plablanec

(75) Inventor: José Miguel Arias López, Tudela (ES)

(73) Assignee: Plantas de Navarra, S.A. (ES)

( * ) Notice: Subject to any disclaimer, the term of this patent is extended or adjusted under 35 U.S.C. 154(b) by 0 days.

(21) Appl. No.: 10/185,655

(22) Filed: Jun. 27, 2002

(65) Prior Publication Data

US 2003/0084492 P1 May 1, 2003

(30) Foreign Application Priority Data

Oct. 23, 2001 (EP) ..... 2001/1667

(51) Int. Cl.[7] ..... A01H 5/00

(52) U.S. Cl. ..... Plt./190

(58) Field of Search ..... Plt./190

*Primary Examiner*—Bruce R. Campell
*Assistant Examiner*—Susan B. McCormick
(74) *Attorney, Agent, or Firm*—Christie, Parker & Hale, LLP

(57) ABSTRACT

A new and distinct variety of Nectarine tree characterized by its low chilling requirement, very early ripening season and highly attractive, good quality, white fleshed, medium-high firm fruit.

3 Drawing Sheets

Classification: The present invention relates to a new *Prunus persica* (L.) Batsch—Nectarine.

Variety denomination: The new plant has the varietal denomination 'Plabanec'.

BACKGROUND OF THE INVENTION

The new variety of Nectarine tree was created in a breeding program by crossing two parents; in particular, by crossing as seed parent a variety designated '88-011' (unpatented) and as pollen parent a variety designated '88-052' (unpatented). Both, female and male, are components of a parent collection from a selection made between plants issued from seeds got in a free pollination in a population of different origin done in 1988. Both parental varieties are property and have not been commercialized.

The seeds resulting from this controlled hybridization were germinated in a greenhouse in the spring of 1997 and planted in a field on the farm of La Mogalla in Cartaya (Huelva), Spain, 7° W., 37° N., 45 feet elevation. The seedlings fruited during the spring of 1999 and one designated as '97.14.065-NB' (unpatented) was selected for its low chilling requirement (250 to 300 hours), its very early ripening season, attractive fruit shape and color, white flesh, medium-high firm, good quality fruit. During 1999, the original plant selection was propagated asexually, at the above noted location, by budding onto standard Peach rootstock variety designated 'GF-677' (non patented) and a test plot of 4 plants was established.

The new variety has been asexually multiplied several times since 1999 at this location by budding onto the standard Peach rootstock variety designated as 'GF-677' (unpatented) and no incompatibility with Peach rootstock has occurred following budding. During all asexual reproduction, the characteristics of the original plant have been maintained and no aberrant phenotypes have appeared.

SUMMARY OF THE INVENTION

The new variety of Nectarine tree differs from its parents and other known cultivars of Nectarine Trees by producing clingstone fruits with a very early ripening date and low chilling requirement (250 to 300 hours). Fruits of the new variety are ripe for commercial harvesting and shipment between approximately April 15$^{th}$ to April 25$^{th}$. These harvesting dates are approximately 20 days earlier than the harvest dates of the commercial Nectarine variety 'Earliglo' (U.S. Plant Pat. No. 7,402) and approximately 20 to 25 days earlier than the harvest dates of the commercial Nectarine variety 'Mayglo' (U.S. Plant Pat. No. 5,245)

COMPARISON WITH OTHER VARIETIES

'Plablanec' produces rounded, slightly flat shaped, small fruit; whereas fruit of 'Earliglo' are larger and more rounded and have a more pronounced suture.

The fruit surface of 'Plablanec' is covered approximately 95% with a red color and its ground color is yellow-green; whereas of the fruit surface of 'Mayglo' is covered approximately 75% to 85% and its skin ground color is yellow.

The new variety differs from 'Mayglo' by producing white fleshed, sweet fruits with a low skin cracking susceptibility.

BRIEF DESCRIPTION OF THE DRAWINGS

The accompanying photographic illustrations show typical specimens of the new variety in color as nearly true as is reasonably possible to make in illustrations of this character.

DESCRIPTION OF THE NEW VARIETY

Figure 1:
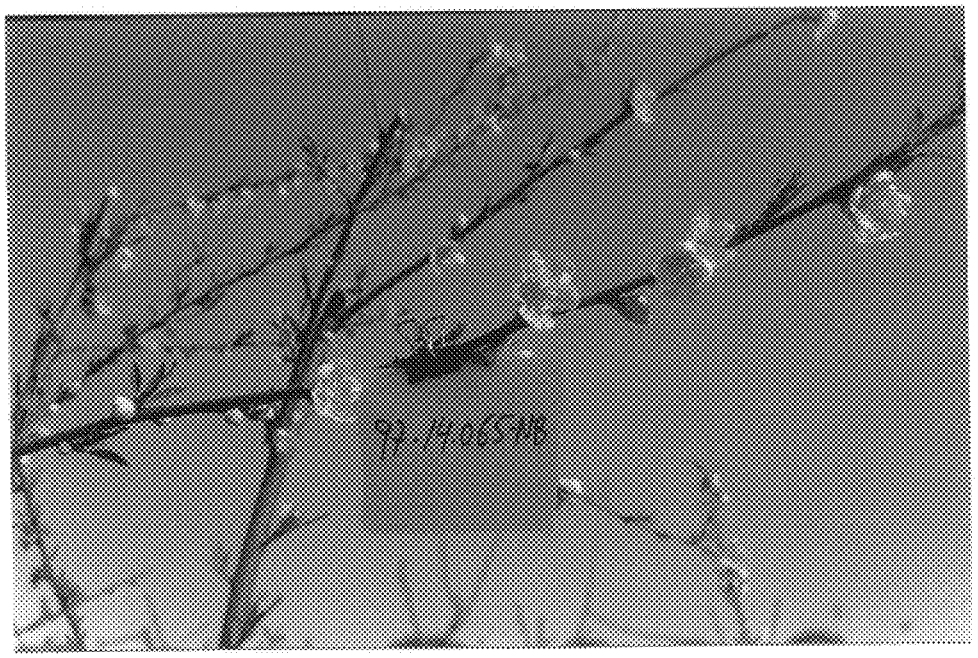
FIG. 1 shows typical flowers of the new variety.
Figure 2:
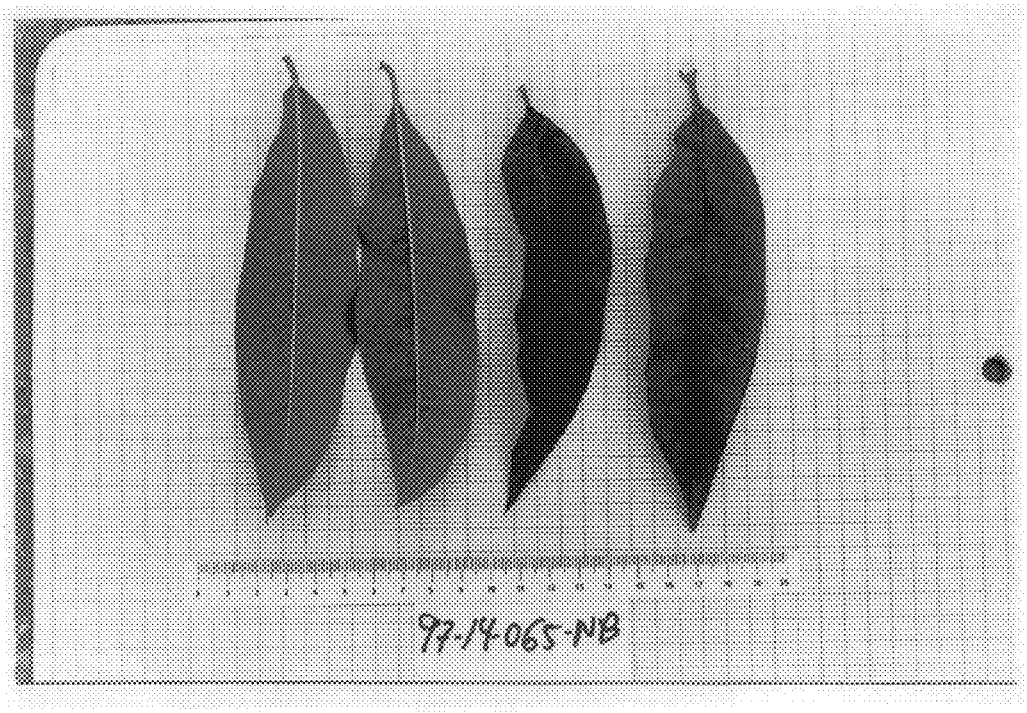
FIG. 2 shows the coloration of the dorsal and ventral leaves of the new variety.
Figure 3:
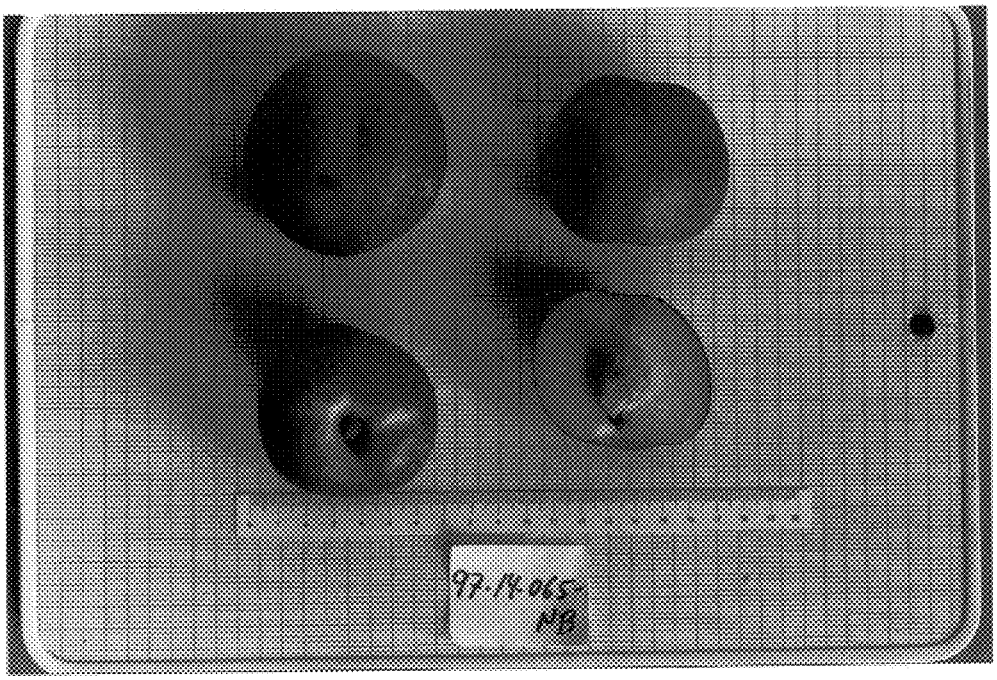
FIG. 3 shows the external coloration of fruits of the new variety when sufficiently matured for harvesting and shipment and one fruit of the new variety dissected in the equatorial plane to illustrate the flesh and stone characteristics.

The following observations and descriptions are of plants grown at the orchard previously described, located near the town of Cartaya, Huelva, Spain. Observations were made of the original seedling tree on its own root during the growing years of 1999 to 2001. Seed was germinated in the Spring of 1997 and the tree was planted in a field in December 1997. Fruit was first observed in the Spring of 1999.

In this description, it is to be understood that references of the dimensions, sizes, colors, etc. of the botanical and phonological characteristics of the new variety are approximations of averages set forth as accurately as practical. Phenotypic expression may vary with light intensity and cultural and environmental conditions. The color references used in this description, are to The Royal Horticultural Society Colour Chart (R.H.S.C.C.) and terminology used in the color descriptions herein refers to plate numbers in said color chart.

Tree:

*Size.*—Average to above-average when compared to other common Nectarine cultivars.

*Productivity.*—Approximately 17000 Kgrs/Ha.

*Form.*—Upright to upright, spreading.

*Height.*—Original seedling reached approximately 3.25 m at end of 2001 growing season.

*Width.*—Original seedling reached approximately 1.70 m at end of 2001 growing season.

*Current season growth.*—Approximately 0.80 to 1.0 m.

*Regularity of bearing.*—Regular.

Trunk:

*Thickness.*—Approximately 110 mm.

*Diameter.*—Approximately 15 cm at end of 2001 growing season when measured at a distance above soil level.

*Bark texture.*—Moderately rough with numerous scarf skin and flat oval lenticels present.

*Bark coloration.*—Grey Group near 201B to 201A.

Branches:

*Size.*—Medium for the species. Diameter: Measured about 63.4 mm during $3^{rd}$ year after grafting.

*Surface texture.*—Average. Current Season Shoots: Substantially glabrous. Color: Greyed-green Group near 191C to 191B.

*Mature branches.*—Appearing furrowed on several year old wood. Color: Greyed-green Group near 197B to 197A.

Leaf:

*Size.*—Considered average for species; measurements taken from vigorous, upright, current season growth at approximately midshoot. Length: Approximately 148 to 180 mm. Width: Approximately 44 to 58 mm. Thickness: Approximately 1 to 2 mm.

*Venation.*—Pinnately net veined; color of mid-vein near 149D to 150D.

*Base shape.*—Slightly oblique.

*Form.*—Lanceolate.

*Tip form.*—Acuminate.

*Color.*—Upper Side: Yellow-green Group near 146A to 148A. Underside: Yellow-Green Group near 148C to 148A.

*Texture.*—Glabrous.

*Margins.*—Crenate, considered generally uniform.

*Leaf petiole.*—Considered medium-long. Length: Approximately 8 to 14 mm. Diameter: Approximately 1 to 2 mm.

*Leaf glands.*—Reniform; generally 2 per side. Length: Approximately 1 to 2 mm. Width: Approximately 0.1 to 0.4 mm.

*Sepals.*—Length about 9 mm, width about 6 mm; usually 5 sepals per flower; color between 178A to 181A.

Inflorescence:

*Flower bud.*—Length about 8 mm, diameter about 3 mm; shape ovoid; color between 177B to 117A.

*Flowers.*—Bloom occurs prior to vegetative bud break; solitary to occasional double individual flowers at a single node; perfect self-fertile.

*Blooming time.*—Considered very early in relation to other Nectarine cultivars.

*Date of bloom.*—First, January $11^{th}$; Full, January $18^{th}$. Flower Diameter: Approximately 39 to 45 mm at full bloom.

*Flower pedicel.*—Length about 4 mm, diameter about 2 mm; color near 144D.

*Bloom quantity.*—Considered very abundant.

*Petalage.*—Considered medium for the species. Length: Approximately 14 to 18 mm. Width: Approximately 14 to 18 mm. Shape: Rounded. Petal Count: Nearly always 5. Texture: Glabrous. Color: Near 65D; abaxial color of petal between 69D to 65D. Apex: Petal apices appear domed.

*Stamens.*—Numerous with pollen present; fertile and abundant.

Reproductive organs:

*Anthers.*—Length about 1 to 1.5 mm, width about 1 mm; color between 185B to 185A.

*Pollen production.*—Pollen is abundant, color between 26B to 26A.

*Filaments.*—Length about 14 mm; color between 69C to 69A, darkening with advanced maturity.

*Pistil.*—About 16 mm, including the ovary, surface texture glabrous, color near 149D.

Fruit: In firm ripe condition at full commercial maturity, first fruit picked on approximately April $15^{th}$; last pick of same fruit in 2001 was approximately April $25^{th}$ in Cartaya, Huelva, Spain conditions.

*Size.*—Medium; uniform. Cheek Diameter: Approximately 60 to 62 mm. Suture Diameter: Approximately 59 to 61 mm. Axial diameter: Average about 56 to 58 mm.

*Form.*—Rounded, slightly flat; generally uniform.

*Suture.*—Extending from base to apex, suture appears as a very thin line at same level as skin.

*Stem cavity size.*—Considered medium for the species. Width: Approximately 23 to 26 mm. Length: Approximately 25 to 30 mm. Depth: Approximately 8 to 11 mm. Form: Rounded. Fruit Base: Concave, rounded in form and uniform. Fruit Apex: Slightly depressed.

*Fruit skin.*—Average in thickness. Surface Texture: Very glabrous. Skin Acidity: Neutral.

*Tenacious to flesh.*—Yes; at commercial maturity.

*Tendency to crack.*—Not observed. Skin Color: Approximately 95% of fruit surface covered with a brilliant Red Group near 53A to 46A; approximately 5% of fruit surface has a yellow-green color group near 150D to 150C.

*Firmness.*—3 to 4 $Kg/cm^2$ =Resistance to penetration measured in Kilograms ($Kg/cm^2$) obtained by Penetrometer ROZE Mod. Arbelette, with a 50 $mm^2$ section head.

*Flesh color.*—Yellow-green Group near 149D to 150D.

*Flesh fibers.*—Numerous, fine and red light colored fibers present at maturity throughout the flesh.

*Flesh texture.*—Generally melting.

*Flavor.*—Considered sweet; soluble solids as °Brix 13.

*Aroma.*—Pleasant and abundant.

*Eating quality.*—Very good to excellent; well above average when compared to other common commercial varieties.

*Stone.*—Attachment: Clingstone at full commercial maturity. Stone Size: Medium for the species. Length: Approximately 26 to 29 mm. Width: Approximately 23 to 25 mm. Thickness: Approximately 17 to 20 mm. Stone Form: Slightly oval. Stone Color: Yellow-Orange Group near 19B to 20B. Tendency to Split: Yes; slightly. Kernel: Form is ovoid. Length: Approximately 15 to 18 mm. Width: Approximately 11 to 13 mm.

Keeping quality: Fruit stored well up to 15 days after harvest at temperatures of about 1° C.

Resistance to insects and disease: No particular susceptibilities were noted.

Shipping quality: Well above average.

Hardiness: No winter injury has been observed in the years of evaluation in the South of Spain, drought and heat tolerance not known.

The new variety of Nectarine tree possesses the characteristics described above as a result of the growing conditions prevailing in Cartaya, Huelva, Spain. It is to be expected that variations in these characteristics may occur when farmed in areas with different climatic conditions, different soil types, and/or varying cultural practices.

I claim:

1. A new and distinct variety of Nectarine tree substantially as illustrated and described herein.

* * * * *